United States Patent
Baxter et al.

(10) Patent No.: US 6,465,486 B1
(45) Date of Patent: Oct. 15, 2002

(54) PYRIDYL/QUINOLINYL IMIDAZOLES

(75) Inventors: Ellen W. Baxter, Glenside; Robert E. Boyd, Horsham; John R. Carson; Michele C. Jetter, both of Norristown; Allen B. Reitz, Lansdale, all of PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/524,451

(22) Filed: Mar. 10, 2000

Related U.S. Application Data

(60) Provisional application No. 60/124,296, filed on Mar. 12, 1999.

(51) Int. Cl.[7] .................. A61K 31/47; C07D 401/00; C07D 215/00; C07D 215/16; C07D 211/70
(52) U.S. Cl. .................. 514/311; 514/314; 546/167; 546/165; 546/178; 546/272.7; 546/275.1; 546/341
(58) Field of Search .................. 546/272.7, 275.1, 546/341, 167, 165, 178; 514/341, 311, 314

(56) References Cited

U.S. PATENT DOCUMENTS

| | | | |
|---|---|---|---|
| 3,574,844 A | | 4/1971 | Gardocki et al. |
| 4,882,343 A | * | 11/1989 | Cordi et al. |
| 4,913,207 A | | 4/1990 | Harakon et al. |
| 5,621,113 A | | 4/1997 | Boyd et al. |
| 5,750,720 A | | 5/1998 | Boyd et al. |

FOREIGN PATENT DOCUMENTS

| | | |
|---|---|---|
| JP | 1-242571 | 9/1989 |
| WO | WO92/14453 A1 | 9/1992 |

OTHER PUBLICATIONS

Auger et. al., Preparation of erythromycins as bactericides, CA reference 129:67977z, Bol. 129, No. 6, p. 893, 1998.*
DeGraw et al., Potential Histidine Decarboxylase Inhibitors. II. 3-(4-Imidazolyl)-2-pyridine and piperidinecarboxylates., CA reference 89:109229v, vol. 89, p. 897, 1978.*
C.L.E. Broekkamp, D. Leysen, B.W.M.M. Peeters, and R.M. Pinder, Journal of Medicinal Chemistry, Prospects for Improved Antidepressants, vol.38 (23), 4615.
William E Heydron, Mirtazapine–A Novel Antidepressant Compound Currently Undergoing Clinical Evaluation, Exp. Opin. Invest. Drugs, 1995 4(10):945–954.
Michael D. Meyer, Structure Activity Studies for a Novel Series of N–(Arylethyl)–N–(1,2,3, 4–Tetrahydronaphthalen–1–YLMethyl)–N–Methylamines Possessing Dual 5–HT Uptake Inhibiting and $\alpha_2$–Antagonistic Activities Journal of Medicinal Chemistry, vol. 40, No. 7 pp. 1049–1062.
Michael E. Meyer, Biorganic & Medicinal Chemistry Letters, vol. 5, No. 19 pp2287–2292,1995. Synthesis and pharmacological Characterization of A–80426: A putative Novel Antidepressant Combining $\alpha$—2 Antagonism With 5–HT Uptake Inhibition.
Arthur A. Hancock, Drug Development Research 35:237–245 1995.
Drug Development Research 35:246, 1995.

* cited by examiner

Primary Examiner—Alan L. Rotman
Assistant Examiner—Binta Robinson

(57) ABSTRACT

Certain imidazo pyridines/quinolines of the formula:

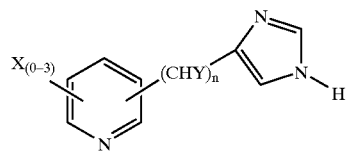

where n is 0, 1, 2;

X is independently selected from the group consisting of $C_{1-4}$alkyl, bromine, chlorine, iodide, trifluoromethyl, $C_{1-4}$alkoxy, —$SO_2NH_2$, nitro, and two adjacent X may be fused to form the moiety:

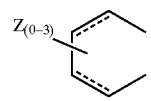

whereby a saturated, partially unsaturated or aromatic six-membered fused ring is formed;

Y is independently selected from the group consisting of hydrogen, hydroxy, $C_{1-4}$alkyl, $C_{1-4}$alkoxy, trifluoromethyl and phenyl; and Z is independently selected from the group consisting of hydroxy, $C_{1-4}$alkyl, bromine, chlorine, iodide, trifluoromethyl, $C_{1-4}$alkoxy, —$SO_2NH_2$ and nitro;

are $\alpha_2$-adrenoceptor modulators which are useful in the treatment of hypertension, glaucoma, sexual dysfunction, depression, attention deficit hyperactivity disorder, Parkinsonism, the need for anesthesia, cardiac arrythmia or the need for analgesia.

4 Claims, No Drawings

PYRIDYL/QUINOLINYL IMIDAZOLES

This application claims the benefit of U.S. provisional application Ser. No. 60/124,296 filed Mar. 12, 1999.

The present invention relates to compounds which bind to the $\alpha_2$-adrenoceptor. More particularly, the present invention relates to certain imidazo pyridines/quinolines which are $\alpha_2$ receptor modulators.

BACKGROUND OF THE INVENTION $\alpha_2$-adrenoceptor modulators are useful to treat a variety of conditions, including, hypertension, glaucoma, sexual dysfunction, depression, attention deficit hyperactivity disorder, Parkinsonism, the need for anesthesia, cardiac arrythmia and the need for analgesia. Particularly, $\alpha_2$-adrenoceptor agonists are well known analgesics. $\alpha_2$-adrenoceptor antagonists have potential as antidepressants in their own right or as adjunct therapies to traditional inhibitors of monoamine reuptake.

Clonidine is a centrally acting $\alpha_2$-adrenoceptor agonist with wide clinical utility as an antihypertensive agent. Clonidine is believed to act by inhibiting the release of norepinephrine from sympathetic nerve terminals via a negative feedback mechanism involving $\alpha_2$-adrenoceptors located on the presynaptic nerve terminal. This action is believed to occur in both the central (CNS) and peripheral (PNS) nervous systems. More recently, the role of $\alpha_2$-adrenoceptor agonists as analgesic agents in humans and antinociceptive agents in animals has been demonstrated. Clonidine and other $\alpha_2$-adrenoceptor agonists have been shown to produce analgesia through a non-opiate mechanism and, thus, without opiate liability. However, other behavioral and physiological effects were also produced, including sedation and cardiovascular effects.

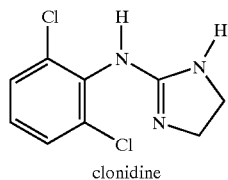

clonidine

Medetomidine, detomidine, and dexmedetomidine are $\alpha_2$-adrenoceptor agonists. Dexmedetomidine is used clinically in veterinary medicine as a sedatives/hypnotic for pre-anaesthesia. These compounds are hypotensive in animals and in humans, but the magnitude of this cardiovascular effect is relatively insignificant.

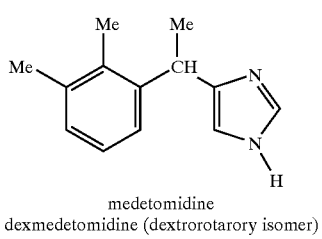

medetomidine
dexmedetomidine (dextrorotarory isomer)

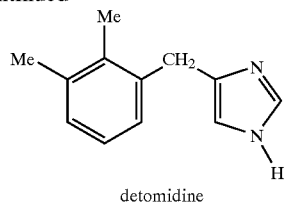

detomidine

U.S. Pat. No. 3,574,844, Gardocki et al., teach 4-[4(or 5)-imidazolylmethyl]-oxazoles as effective analgesics. The disclosed compounds are of the general formula:

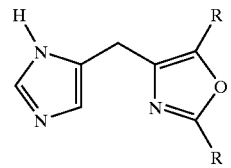

Compounds of this type are insufficiently active and suffer from unwanted side effects.

U.S. Pat. No. 4,913,207, Nagel et al., teach arylthiazolylimidazoles as effective analgesics. The disclosed compounds are of the general formula:

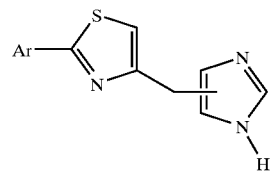

Compounds of this type are insufficiently active and suffer from unwanted side effects.

WO92/14453, Campbell et al., teach 4-[(aryl or heteroaryl)methyl]-imidazoles as effective analgesics. The disclosed compounds are of the general formula:

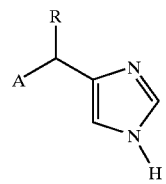

R is H or alkyl
A is aryl or heteroaryl

The disclosed compounds are insufficiently: active and suffer from unwanted side effects.

Kokai No. 1-242571, Kihara et al., disclose a method to produce imidazole derivatives for use, among other uses, as antihypertensive agents.

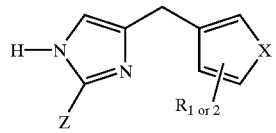

Z is H or phenyl
R is H, alkyl or halogen
X is S or O

A single mixture of compounds meeting the above formula was reportedly produced by the inventive method. This was a mixture of 4-(2-thienyl)-methylimidazole and 4-(3-thienyl)-methylimidazole represented by the following formula:

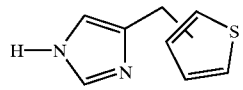

The disclosed compounds are insufficiently active and suffer from unwanted side effects.

U.S. Pat. No. 5,621,113 and U.S. Pat No. 5,750,720, Boyd and Rasmussen disclose certain substituted 2- and 3-thienyl methylimidazoles as effective analgesic agents.

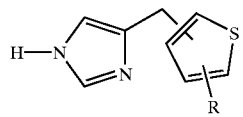

Many potent and selective $\alpha_2$ antagonists, such as idazoxan, have been synthesized and evaluated in limited clinical trials as antidepressants.(*J. Med. Chem.* 1995, 38 (23), 4615.) Mirtazapine is a closely related analog of the established antidepressant mianserin. This compound has been shown to be an antagonist at $\alpha_2$ receptors and exhibits antidepressant activity in vivo. (*Exp. Opin. Invest. Drugs* 1995, 4(10), 945). An agent with the dual profile of a 5 HT reuptake inhibitor and an $\alpha_2$ antagonist might serve to enhance synaptic concentrations of 5-HT relative to that achievable through 5-HT uptake inhibition alone and in turn produce a more effective antidepressant response. A novel series of compounds with such a profile was found to possess putative antidepressant effects in vivo (*J. Med. Chem.* 1997, 40 (7), 1049; *Bioorg. Med. Chem Lett.* 1995, 5, 2287.; *Drug. Dev. Res.* 1995, 35, 237.; *Drug. Dev. Res.* 1995, 35, 246.)

SUMMARY OF THE INVENTION

Briefly, there is provided by the present invention compounds which are $\alpha_2$-adrenoceptor modulators of the formula:

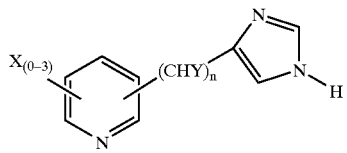

where n is 0, 1, 2;

X is independently selected from the group consisting of $C_{1-4}$alkyl, bromine, chlorine, iodide, trifluoromethyl, $C_{1-4}$alkoxy, —$SO_2NH_2$, nitro, and two adjacent X may be fused to form the moiety:

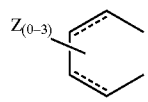

whereby a saturated, partially unsaturated or aromatic six-membered fused ring is formed;

Y is independently selected from the group consisting of hydrogen, hydroxy, $C_{1-4}$alkyl, $C_{1-4}$alkoxy, trifluoromethyl and phenyl; and Z is independently selected from the group consisting of hydroxy, $C_{1-4}$alkyl, bromine, chlorine, iodide, trifluoromethyl, $C_{1-4}$alkoxy, —$SO_2NH_2$ and nitro.

DETAILED DESCRIPTION OF THE INVENTION

The compounds of the present invention are prepared by the methods shown in Schemes 1 to 5. In Scheme 1, heterocyclic carboxylic acid 1 is converted to its Weinreb amide 2 by published procedures (Weinreb and Nahm, *Tetrahedron Letters*, 1981, 22, 3815) which is then reacted with the Grignard reagent derived from $N^1$-trityl-4-iodoimidazole (Turner and Lindell, *J. Org. Chem.* 1991, 56, 5739) to give the ketone intermediate 3. This ketone intermediate 3 could be deoxygenated by reaction with a reagent such as HI to give product 4. Alternatively, as depicted in Scheme 2, the intermediate ketone 3 could be reacted with an alkyl or aryllmagnesium halide (or other Grignard or lithium reagent) to give 5 which is then deoxygenated and deprotected to yield 6. Suitable means of deoxygenation/deprotection include 57% hydriodic acid, hydrogenation using Pd(OH)$_2$ as catalyst, triethylsilane/trifluoroacetic acid, borane/methylsulfide or NaBH$_4$/trifluoroacetic acid.

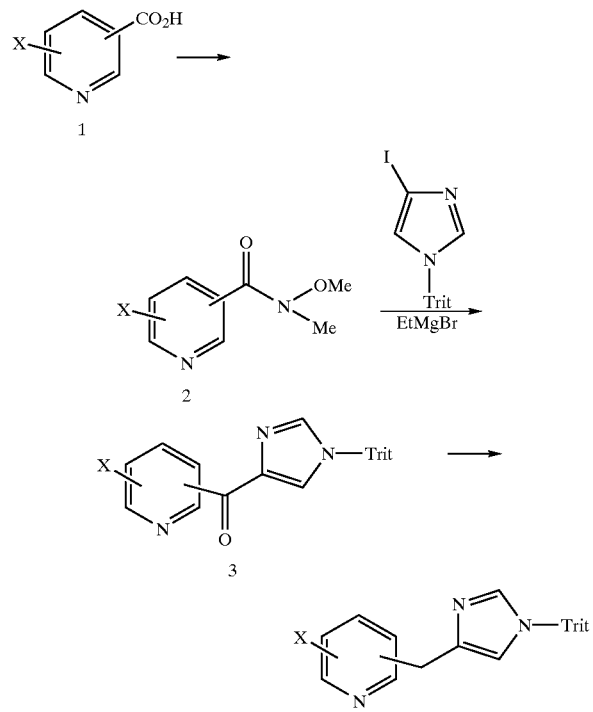

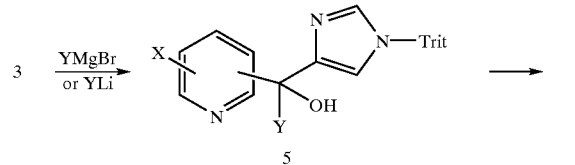

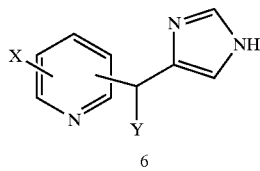

In Scheme 3, heterocyclic aldehyde 7 reacts with the Grignard reagent derived from $N^1$-trityl-4-iodoimidazole (Turner and Lindell, *J. Org. Chem.* 1991, 56, 5739) to yield the heterocyclic hydroxymethylimidazole intermediate 8. This intermediate is deoxygenated and deprotected in one step for example with refluxing HI or another suitable means such as described above to give product 9.

In the case where X is hydrogen, $C_{1-4}$alkyl, $C_{1-4}$alkoxy and trifluoromethyl, the appropriately substituted heterocyclic hydroxyimidazoles 5 or 8 may be produced and the substituent in question will stably endure the reactions of Scheme 2 and Scheme 3 to arrive at target products 6 and 9 respectively. In the case where X is chlorine, bromine, and nitro, the above described deoxygenation-deprotection steps could also be achieved using triethylsilane/trifluoroacetic acid, 57% hydriodic acid or other means such as borane/methylsulfide or $NaBH_4$/trifluoroacetic acid.

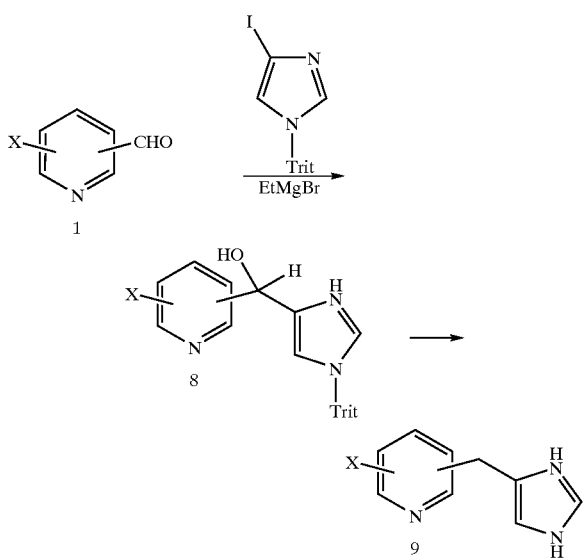

In Scheme 4, heterocyclic carbinol 10 is converted to the bromide by reaction with a brominating agent such as $CBr_4/PPh_3$ or $PBr_3$. The bromide 11 reacts with $PPh_3$ to yield the triphenylphosphonium reagent 12 which undergoes Wittig reaction with $N^1$-tritylimidazole-4-carboxaldehyde in the presence of a suitable base such as NaOMe/MeOH or LiHMDS. The requisite $N^1$-tritylimidazole-4-carboxaldehyde is easily obtained by published procedures (Jetter et al, *Org. Prep. Proc. Intl.* 1996, 28, 709.). The products of the Wittig reaction 13 are deprotected with an acid such as hydrochloric acid, formic acid or trifluoroacetic acid and then reduced by hydrogenation with an appropriate catalyst to yield the target 14.

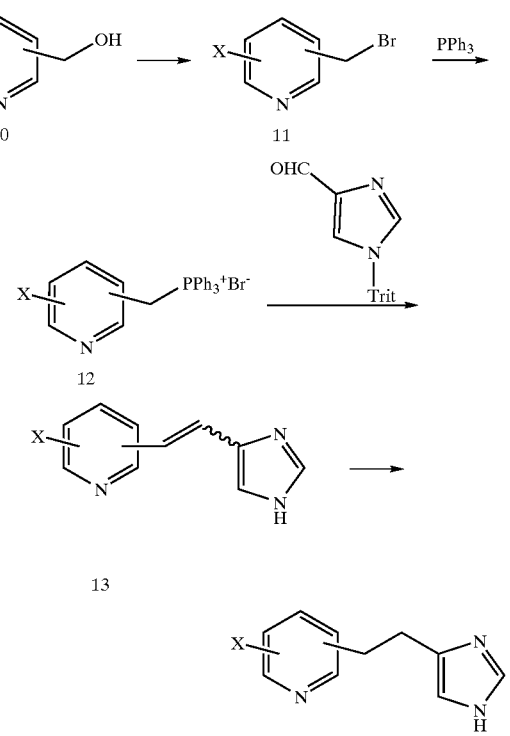

In Scheme 5, hydroxyquinoline 15 is converted to its triflate by reaction with a strong base such as NaH and an appropriate triflating agent such as N-phenyl trifluoromethanesulfonimide to give quinolyl triflate 16. The triflate 16 could be condensed in a Stille coupling reaction with a 4-(stannyl)imidazole reagent in the presence of Pd(0) to give 17, or condensed with the 4-imidazo Grignard reagent described above in the presence of $ZnCl_2$ to also give 17. The tritylated intermediate 17 is then deprotected with acid (HCl, trifluoracetic acid or formic acid) to give the target product 18. Scheme 5 depicts quinoline as the substrate but the same sequence of reactions could be performed on an isoquinoline substrate.

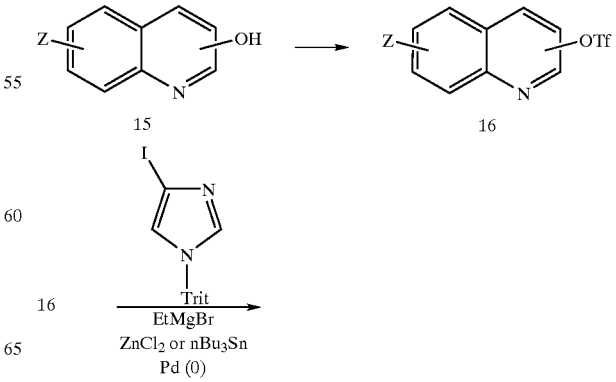

-continued

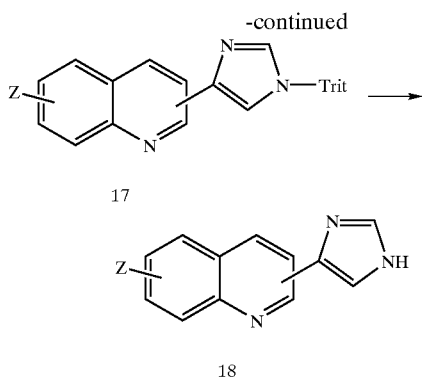

Where the term $C_{1-4}$alkyl is employed, there are included methyl, ethyl, n-propyl, i-propyl, n-butyl, i-butyl and t-butyl. In the case of the term $C_{1-4}$alkoxy, there are included the equivalent —$O(C_{1-4}alkyl)$.

Preferred compounds of the present invention are:

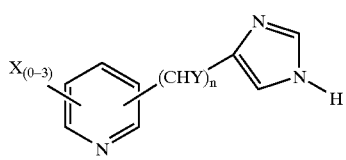

where X, Y, Z and n are dependently selected from the group consisting of:

| position of attachment | X | Y | Z | n |
|---|---|---|---|---|
| 3-pyridyl | 4-Me | H | — | 1 |
| 3-pyridyl | 2-Me | H | — | 2 |
| 3 pyridyl | 5-Me | Me | — | 1 |
| 3-pyridyl | 2-Et | OH | — | 1 |
| 3-pyridyl | 5-isopropyl | OEt | — | 1 |
| 2-pyridyl | 3-Me | H | — | 1 |
| 2 pyridyl | 3-OMe | H | — | 2 |
| 2-pyridyl | 5-Me | H | — | 2 |
| 2-pyridyl | — | Ph | — | 1 |
| 2-pyridyl | 4-Et | Me | — | 1 |
| 2-pyridyl | 3-Br | H | — | 1 |
| 2-pyridyl | 5-OEt | Me | — | 1 |
| 4-pyridyl | — | H | — | 2 |
| 4-pyridyl | 2-Me | H | — | 1 |
| 6-quinolinyl | fused phenyl | H | — | 1 |
| 5-quinolinyl | fused phenyl | — | — | 0 |
| 7-quinolinyl | fused phenyl | H | 8-Me | 1 |
| 8-quinolinyl | fused phenyl | — | — | 0 |
| 4-isoquinolinyl | fused phenyl | H | — | 1 |
| 5-isoquinolinyl | fused phenyl | — | — | 0 |
| 6-quinolinyl | fused phenyl | — | 2-Me | 0 |
| 7-isoquinolinyl | fused phenyl | H | 3-Me | 1 |
| 8-quinolinyl | fused phenyl | Me | — | 1 |
| 2-pyridyl | 5,6-fused cyclohexyl | H | — | 1 |
| 2-pyridyl | 5,6 fused cyclohexyl | H | — | 2 |
| 3-pyridyl | 4,5-fused cyclohexyl | H | — | 1 |
| 3-pyridyl | 4,5-fused cyclohexyl | H | — | 2 |

The compounds of the present invention may be used to treat a medical condition as named herein, such as, mild to moderate pain in warm-blooded animals, such as, humans by administration of an effective dose. The dosage range would be from about 10 to 3000 mg, in particular about 25 to 1000 mg or about 100 to 500 mg, of active ingredient 1 to 4 times per day for an average (70 kg) human although it is apparent that activity of individual compounds of the invention will vary as will the pain being treated. In regard to the use of these $\alpha_2$-adrenoceptor modulators to treat hypertension, glaucoma, sexual dysfunction, depression, attention deficit hyperactivity disorder, the need for anesthesia and cardiac arrythmia, a therapeutically effective dose can be determined by persons skilled in the art by use of established animal models. Pharmaceutical compositions of the invention comprise the formula (I) compounds as defined above, particularly in admixture with a pharmaceutically-acceptable carrier.

To prepare the pharmaceutical compositions of this invention, one or more compounds of the invention or salt thereof as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutically acceptable salts referred to above generally take a form in which the imidazolyl ring is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

Biological Procedures

The activity of compounds of the invention as $\alpha_2$ modulators may be demonstrated by the in vivo and in vitro assays as described below:

Alpha-$_2$D Adrenergic Receptor Binding Assay

Male, Wistar rats (150–250 g, VAF, Charles River, Kingston, N.Y.) are sacrificed by cervical dislocation and their brains removed and placed immediately in ice cold HEPES buffered sucrose. The cortex is dissected out and homogenized in 20 volumes of HEPES sucrose in a Teflon™-glass homogenizer. The homogenate is centrifuged at 1000 g for 10 min, and the resulting supernatant centrifuged at 42,000 g for 10 min. The resulting pellet is resuspended in 30 volumes of 3 mM potassium phosphate buffer, pH 7.5, preincubated at 25° C. for 30 min and recentrifuged. The resulting pellet is resuspended as described above and used for the receptor binding assay. Incubation is performed in test tubes containing phosphate buffer, 2.5 mM $MgCl_2$, aliquots of the synaptic membrane fraction, the ligand $^3$H-para-aminoclonidine and test drug at 25° C. for 20 min. The incubation is terminated by filtration of the tube contents through glass fiber filter sheets. Following washing of the sheets with 10 mM HEPES buffer, the adhering radioactivity is quantified by liquid scintillation spectrometry.

Binding of the test drug to the receptor is determined by comparing the amount of radiolabeled ligand bound in control tubes without drug to the amount of radiolabeled ligand bound in the presence of the drug. Dose-response data are analyzed with LIGAND, a nonlinear curve fitting program designed specifically for the analysis of ligand binding data. This assay is described by Simmons, R. M. A., and Jones, D. J., Binding of [$^3$H-]prazosin and [$^3$H-]p-aminoclonidine to α-Adrenoceptors in Rat Spinal Cord, *Brain Research* 44 5:338–349, 1988.

Mouse Acetylcholine Bromide-Induced Abdominal Constriction Assay (MAIT)

The mouse acetylcholine bromide-induced abdominal constriction assay, as described by Collier et al. in Brit. J. Pharmacol. Chem. Ther., 32: 295–310, 1968, with minor modifications was used to assess analgesic potency of the compounds herein. The test drugs or appropriate vehicle were administered orally (p.o.) and 30 minutes later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to a nociceptive, stimulus (equated to % analgesia) was calculated as follows: The % Inhibition of response, i.e., % analgesia is equal to the difference between the number of control animals responding and the number of drug-treated animals responding times 100 divided by the number of control animals responding.

At least 15 animals were used for control and in each of the drug treated groups. At least three doses were used to determine each dose response curve and $ED_{50}$ (that dose which would produce 50% analgesia). The $ED_{50}$ values and their 95% fiducial limits were determined by a computer assisted probit analysis.

Biological Data

Table 1 lists certain biological data of the compounds made in the examples below wherein the position of attachment of the imidazole-containing side chain and variables X, Y and n are thus indicated.

TABLE 1

| Cpd # | position of attachment | X | Y | n | % inh of $\alpha_{2D}$ $K_i$ (nM) | MAIT |
|---|---|---|---|---|---|---|
| Cp-1 | 3-pyridyl | 2-Me | H | 1 | 7.1 | 93 po |
| Cp-2 | 3-pyridyl | 2-Me | Me | 1 | 28.8 | 33 po |
| Cp-3 | 3-pyridyl | — | H | 1 | 89% | 47 po |
| Cp-4 | 3-pyridyl | 5-Br | H | 1 | 83% | 54 po |
| Cp-5 | 3-pyridyl | 5-Br | Me | 1 | 5.4 | 53 po |
| Cp-6 | 2-pyridyl | — | H | 1 | 83% | 40 po |
| Cp-7 | 2-pyridyl | — | Ph | 1 | 1000 | 13 po |
| Cp-8 | 2-pyridyl | — | H | 2 | 100% | 7 sc |
| Cp-9 | 2-quinolinyl | Fused Phenyl | H | 1 | 1.6 | 20 po |
| Cp-10 | 4-isoquinolinyl | Fused Phenyl | — | 0 | 159 | 27 po |
| Cp-11 | 6-quinolinyl | Fused Phenyl | — | 0 | 81% | 27 po |
| Cp-12 | 7-quinolinyl | Fused Phenyl | — | 0 | 84% | 7 po |

The following Examples demonstrate synthesis of the compounds herein:

EXAMPLE 1

4-[(2-Methylpyrid-3-yl)methyl]-1H-imidazole Dihydrochloride (RWJ-53780-002-A)

To a solution of 2-methylnicotinic acid (5.00 g, 36.4 mmol) in 100 mL of dry dichloromethane was slowly added 1,1'-carbonyldiimidazole (5.91 g, 36.4 mmol) under nitrogen. The mixture was stirred for 10 minutes, and then N,O-dimethylhydroxylamine hydrochloride (5.91 g, 36.4 mmol) was added. After 20 h, the reaction mixture was diluted with chloroform (100 mL). The resulting solution was washed with aqueous NaOH (1 N) solution, dried ($NaSO_4$), and concentrated to give 6.45 g of a yellow oil. This material was purified on flash silica gel (1% methanol-chloroform) to provide the desired product as 3.07 g (47%) of a colorless oil. MS (ES), m/z 181 (MH$^+$). $^1$H NMR ($CDCl_3$) δ 2.57 (s, 3H), 3.36 (br s, 3H), 3.46 (br s, 3H), 7.17 (dd, J=7.6, 5.0 Hz, 1H), 7.61 (dd, J=8.0, 1.1 Hz, 1H), 8.54 (dd, J=5.0, 1.3 Hz, 1H).

To a solution of 4-iodo-1-tritylimidazole (6.88 g, 15.8 mmol) in 65 mL anhydrous dichloromethane was added 6.3 mL of a solution of ethyl magnesium bromide (3.0 M, 18.9 mmol) in diethyl ether under argon. The reaction mixture was stirred for 2.5 h, and then a solution of N-methoxy, N-methyl-2-methylnicotinamide (2.84 g, 15.8 mmol) was added. After 5 days of stirring, the reaction mixture was poured into saturated aqueous ammonium chloride solution (125 mL). The layers were separated, and the aqueous layer was extracted twice with dichloromethane (50 mL). The organic extracts were combined, dried ($Na_2SO_4$), and concentrated to provide a red-orange foam which was purified on flash silica gel (1% methanol-chloroform to 2% methanol-chloroform) to provide the desired product as 5.56 g (82%) of a golden-brown foam. MS (PB-$NH_3$), m/z 430 (MH$^+$). $^1$H NMR ($CDCl_3$) δ 2.63 (s, 3H), 7.02–7.16 (m, 7H), 7.19 (dd, J=7.8, 5.1 Hz, 1H), 7.28–7.41 (m, 8H), 7.49 (d, J=0.9 Hz, 1H), 7.70 (d, J=0.9 Hz, 1H), 7.96 (dd, J=7.9, 1.2 Hz, 1H), 8.57 (dd, J=7.9, 4.9 Hz, 1H.

Following a literature procedure (Bolitt, V.; Mioskowski, C.; Reddy, S. P.; Falck, J. R. *Synthesis* 1988, 388), a solution of 4-(1-tritylimidazolyl) 3-(2-methylpyridyl) ketone (0.38 g, 0.885 mmol) in hydriodic acid (10 mL, 57%) was refluxed 18 h. After cooling, the reaction mixture was slowly poured into an ice-cold saturated aqueous solution of sodium hydrogensulfite (75 mL). The resulting mixture was extracted three times with diethyl ether (20 mL). The aqueous solution was then made basic by slowly adding solid sodium carbonate, and then chloroform (75 mL) was added. The resulting mixture was passed through a sintered glass funnel. The layers of the filtrate were separated, and the aqueous layer was extracted twice with chloroform (25 mL). The chloroform extracts were combined, washed twice with saturated aqueous sodium carbonate solution (25 mL), water (25 mL), and brine (25 mL), and then dried ($Na_2SO_4$) and concentrated to provide 0.100 g of a colorless glass.

Following the procedure described above, a solution of 4-(1-tritylimidazolyl) 3-(2-methylpyridyl) ketone (2.67 g, 6.22 mmol) in hydriodic acid (70 mL, 57%) was refluxed 20 h. After cooling, the reaction mixture was slowly poured into an ice-cold saturated aqueous solution of sodium hydrogensulfite (200 mL). The resulting mixture was extracted three times with diethyl ether (50 mL). The aqueous solution was then made basic by slowly adding solid sodium carbonate, and then chloroform (200 mL) was added. The resulting mixture was passed through a sintered glass funnel. The layers of the filtrate were separated, and the aqueous layer was extracted twice with chloroform (50 mL). The chloroform extracts were combined, washed twice with saturated aqueous sodium carbonate solution (100 mL), water (100 mL), and brine (100 mL), and then dried ($Na_2SO_4$) and concentrated to provide 0.63 g of a cream-colored solid. This material was combined with 0.100 g of the colorless glass described previously and dissolved in diethyl ether, and 12 N hydrochloric acid (0.70 mL) was added. A beige precipitate came out of solution. Recrystallization from methanol and diethyl ether gave 0.35 g (19%) of 4-[(2-methylpyrid-3-yl)methyl]-1H-imidazole dihydrochloride as a cream-colored powder, mp 236–237.5° C. $^1$H NMR (DMSO-$d_6$) δ 2.77 (s, 3H), 4.27 (s, 2H), 7.50 (s, 1H), 7.84 (dd, J=7.5, 6.1 Hz, 1H), 8.35 (d, J=7.9 Hz, 1H), 8.68 (d, J=5.7 Hz, 1H), 9.10 (s, 1H).

Elemental analysis: Calculated for $C_{10}H_{11}N_3.2HCl.0.6H_2O$: C, 46.74; H, 5.57; N, 16.35; Cl, 27.59; $H_2O$, 4.20. Found C, 46.70; H, 5.54; N, 16.56; Cl, 27.49; $H_2O$, 4.46.

EXAMPLE 2

Cp-2

4-[(2-Methylpyrid-3-yl)ethyl]-1H-imidazole Dihydrochloride (RWJ-53862-002-A)

To a solution of 4-(1-tritylimidazolyl) 3-(2-methylpyridyl) ketone (2.20 g, 5.12 mmol) in 60 mL of anhydrous THF was added methyl magnesium bromide (3.0 M, 7.68 mmol) in diethyl ether under argon. The reaction mixture was stirred for 3 days and was then poured into saturated aqueous ammonium chloride solution. The layers were separated, and the aqueous solution was extracted three times with ethyl acetate (50 mL). The ethyl acetate extracts were combined, dried ($Na_2SO_4$), and concentrated to provide 1.27 g of the desired carbinol as a beige foam. MS (PB-$NH_3$), m/z 446 (MH$^+$). $^1$H NMR (CDCl$_3$) δ 1.84 (s, 3H), 2.33 (s, 3H), 3.13 (br s, 1H), 6.64 (s, 1H), 7.02–7.19 (m, 8H), 7.28–7.38 (m, 8H), 7.42 (d, J=1.1 Hz, 1H), 7.92 (dd, J=6.8 Hz 1H), 8.57 (dd, J=4.9 Hz, 1 H).

The carbinol was deoxygenated according to the procedure of Example 1 to provide 0.35 g (24%) of 4-[(2-methylpyrid-3-yl)ethyl]-1H-imidazole dihydrochloride as a cream-colored powder, mp 258.5–263° C. $^1$H NMR (DMSO-$d_6$) δ 1.62 (d, J=7.0 Hz, 3H), 2.85 (s, 3H), 4.62 (q, J=7.0 Hz, 1H), 7.65 (s, 1H), 7.80 (br t, J=6.8 Hz, 1H), 8.18 (d, J=7.8 Hz, 1H), 8.66 (d, J=5.3 Hz, 1H), 9.09 (s, 1H). Elemental analysis: Calculated for $C_{11}H_{13}N_3.2HCl$: C, 50.78; H, 5.81; N, 16.15. Found C, 50.41; H, 5.72; N, 15.95.

EXAMPLE 3

Cp-3 was prepared in an analogous manner to Cp-1 to yield 4-[pyridinyl-3-yl)methyl]-1H-imidazole dihydrochloride as 0.04 g (0.7%) of a fluffy white powder, mp 215–230.5° C. $^1$H NMR (DMSO-$d_6$) δ 4.30 (s, 2H), 7.52 (s, 1H), 7.95 (dd, J=7.8 Hz, 1H), 8.43 (d, J=7.8 Hz, 1H), 8.81 (d, J=5.2 Hz, 1H), 8.92 (s, 1H), 9.08 (s, 1H).

Cp-4 was prepared in an analogous manner to Cp-1 to yield 4-[(5-Bromopyridin-3-yl)methyl]-1H-imidazole Fumarate, 0.34 g, 24%, mp 139–145 ° C.

Cp-6 was prepared in an analogous manner to Cp-1 to yield 4-[(Pyridin-2-yl)methyl]-1H-imidazole Hydrochloride, 0.25 g, 22%, mp 197–200 ° C.

EXAMPLE 4

Cp-5 was prepared in an analogous manner to Cp-2 to yield 4-[(5-Bromopyridin-3-yl)ethyl]-1H-imidazole Fumarate, 1.12 g, 52%, mp 156–158 ° C.

Cp-7 was prepared in a manner analogous to Cp-2 to yield 4-[(Pyridin-2-yl)methylphenyl]-1H-imidazole, 0.26 g, 20%, mp 180–182 ° C.

EXAMPLE 5

Pyridyl-2-carbinol (0.02 moles) was dissolved in 50 mL of $CH_2Cl_2$ and $CBr_4$ (0.03 moles) was added. The clear reaction mixture was then cooled to 0° C. (ice bath). Triphenylphosphine (0.03 moles) was then slowly added and the dark yellow-orange reaction mixture was stirred at 0° C. for an additional 2 hours. Saturated $NaHCO_3$ (30 mL) was added to the reaction mixture and the $CH_2Cl_2$ layer was separated. The organic layer was washed with brine (30 mL), dried over $Na_2SO_4$ and evaporated under reduced pressure. The residue was chromatographed on silica gel eluting with $CH_2Cl_2$:1% MeOH to yield the product as a yellow oil, 2.77 g (80%). $^1$H NMR (CDCl$_3$): δ 4.55 (s, 2H), 7.2 (t, 1H), 7.45 (d, 1H), 7.7 (t, 1H), 8.6(d, 1H).

2-Bromomethyl pyridine (0.01 moles) was dissolved in 50 mL of THF and PPh$_3$ (0.01 moles. 1.0 equivalents) was added. The reaction mixture was heated at reflux for 1 hour. The reaction mixture was filtered while hot and the precipitated solid was collected by filtration. The solid was washed with THF and air-dried. The product (off-white solid), 3.9 g (90%) was used in the next reaction without further purification.

$^1$H NMR (CDCl$_3$): δ 5.7 (d, 2H ), 7.6–8.1 (m, 19H).

The phosphonium salt (0.005 moles) was dissolved in 30 mL of methanol and sodium methoxide in methanol was added (0.006 moles, 1.2 equivalent). To this solution was added $N^1$-tritylimidazole-4-carboxaldehyde (0.005 moles, 1.0 equivalent) and the reaction mixture was allowed to stir at room temperature for 30 minutes. The reaction mixture was then heated at reflux for 16 hours. The reaction mixture was cooled and the solvent was evaporated under reduced pressure. The residue was taken up in $CH_2Cl_2$, washed with saturated $NH_4Cl$, dried over $Na_2SO_4$ and evaporated under reduced pressure. The product was purified by chromatography on silica gel eluting with 50:50 hexane/ethyl acetate.

The product was obtained as an off-white solid, 1.34 g (67%). $^1$H NMR (CDCl$_3$): δ 7.2–7.7 (m, 23H). These compounds (mixture of cis and trand isomers) were then taken on for deprotection.

Deprotection:

The product above (0.004 mole) was dissolved in 20 mL of methanol (did not dissolve completely) and 1.5 mL of concentrated HCl was added. The clear solution was heated at reflux for 16 hours. The reaction mixture was cooled and the solvent was evaporated under reduced pressure. Methanol was added to the oily residue and evaporated 2 additional times. The residue was twice triturated with ether to remove the trityl byproduct. The solid was collected and then dissolved in 10 mL of H$_2$O. This solution was basified by the addition of solid Na$_2$CO$_3$ and extracted with 15 mL of ether. The ether layer was dried over K$_2$CO$_3$ and evaporated to a tan oil. This oil was characterized by $^1$H NMR to be composed of predominantly the trans isomer. $^1$H NMR (CDCl$_3$): δ 7.1–7.3 (m, 3H), 7.4–7.8 (m, 4H), 8.5 (d, 1H).

Reduction

The mixture of pyridyl alkenyl imidazoles (0.003 mole) was dissolved in 20 mL of methanol. To this solution was added 250 mg of 10% Pd/C. The reaction mixture was hydrogenated at 45 psi for 5 hours. The reaction mixture was filtered through Celite and the solvent was evaporated under reduced pressure. CH$_2$Cl$_2$ (10 mL) was added to the residue and evaporated. $^1$H NMR (CD$_3$OD): δ 2.9 (t, 2H), 3.1 (t, 2H), 6.7 (s, 1H), 7.15 (s, 1H), 7.2 (s, 1H), 7.5 (s, 1H), 7.6 (m, 1H), 8.4 (d, 1H). Maleic acid (2.0 equivalents) were added to the residue to form the maleate salt, which is Cp-8. The product was obtained as an off-white solid, mp 125–126° C.

$^1$H NMR (CD$_3$OD): δ 3.2 (bs, 4H), 6.35 (s, 2H), 7.2 (s, 1H), 7.3–7.4 (m, 2H), 7.8 (t, 1H), 8.5 (d, 1H), 8.8 (s, 1H).

EXAMPLE 6

Cp-9

To a solution of N-triphenylmethyl-4-iodo-imidazole (8.7 g, 20.0 mmol) in THF (50 mL) was added 3.0 M MeMgBr in Et2O (7.0 mL, 21.0 mmol) and the mixture was stirred at room temperature. When the starting material had been consumed as judged by TLC, a solution of quinoline-2-carboxaldehyde (3.3 g, 21,0 mmol) in THF (25 mL) was added dropwise. The reaction was stirred 1 hr at room temperature and then quenched with NH$_4$Cl and extracted with EtOAc. The aqueous layer was extracted with a second portion of EtOAc. The extracts were combined and washed with water and then brine and then dried over Na$_2$SO$_4$. The solution was filtered and the solvent was evaporated in vacuo. The residue was chromatographed on silica (99.5:0.5 CHCl$_3$/10% NH$_4$OH in MeOH) to give a light yellow oil (5.8 g, 70%) which crystallized on standing. $^1$H NMR and Mass spec are consistent with the assigned structure (4-[N-Triphenylmethyl-(2-quinolinyl)-1H-imidazole]-methanol).

To 48% HI (35 mL) was added 4-[N-Triphenylmethyl-(2-quinolinyl)-1H-imidazole]-methanol (1.0 g, 2.1 mmol) and the mixture was heated at reflux under Ar. After 24 hr the reaction was allowed to cool to room temperature and then poured onto a mixture of ice/NaHSO$_3$. The solution was basified with solid Na$_2$CO$_3$ and extracted 2× with CHCl$_3$. The extracts were combined and washed with water and then brine and then dried over K$_2$CO$_3$. The solution was filtered and the solvent was evaporated in vacuo and the residue was chromatographed on silica (97.5:2.25:0.25 CHCl$_3$/MeOH/NH$_4$OH) to give the desired product (0.27 g, 62%). This was combined with 150 mg of fumaric acid in 2-PrOH. The solvent was evaporated in vacuo and the residue was recrystallized from acetone to give Cp-9 (0.217 g) mp 168–170° C. (dec).

EXAMPLE 7

Cp-10

NaH (0.88 g, 0.02 moles) was washed with 10 mL of hexane and then suspended in 100 mL dry THF. The 5-hydroxyisoquinoline (2.9 g, 0.02 moles) was added in portions and the reaction mixture was stirred at room temperature for 1 hour. A solution of N-phenyltriflimide (7.1 g, 0.02 moles) in 15 mL of THF was added to the cloudy yellow reaction mixture. After the addition, the now clear reaction mixture was stirred for 2 hours at room temperature. The solvent was evaporated under reduced pressure. The residue was taken up in 40 mL of CH$_2$Cl$_2$, washed twice with 20 mL 1 N NaOH, then 25 Ll of brine, dried over Na$_2$SO$_4$ and evaporated under reduced pressure. The product (5.0 g, 90%) was isolated as a beige solid and used without further purification. $^1$H NMR (CDCl$_3$) δ 7.8 (m, 2H), 8.1 (d, 1H), 8.3 (d, 1H), 8.7 (d, 1H), 9.6 (s, 1H).

Ethyl magnesium bromide (4.0 mL of 3.0 M solution in diethyl ether. 0.012 mole) was added to a solution of 1-trityl-4-iodoimidazole (2.52 g, 0.01 mole) in 50 mL of THF (or CH$_2$Cl$_2$). The reaction mixture was stirred at room temperature for 45 min at which time TLC (70:30 hexane/ethylacetate) indicated that starting material was consumed. Tributyltin chloride was added and the reaction mixture was stirred for an additional 2 hrs. The solvent was evaporated under reduced pressure and the residue was chromatographed on silica gel eluting with hexane. The 4-imidazole stannane which was obtained was a thick colorless oil which solidified under vacuum (5.2 g, 87%). $^1$H NMR (300 MHz, CDCl$_3$) δ 0.8–1.05 (m, 9H), 1.3–1.4 (m, 12H), 1.5 (m, 6H), 6.75 (s, 1H), 7.1–7.2 (m, 6H), 7.4–7.5 (m, 9H), 7.6 (s, 1H).

The isoquinolinyl triflate prepared above (1.66 g, 0.006 mole) was dissolved in 75 mL of dioxane and added via syringe to a solution of the imidazole stannane (2.99 g, 0.005 mole) in 10 mL of dioxane. Lithium chloride (0.76g, 0.018 mole) was added, the reaction mixture was degassed by bubbling N$_2$ through the reaction mixture for 30 minutes and then tetrakis(triphenylphosphine) palladium (0) (0.347 g, 0.0003 mole) was added. The reaction mixture was heated to reflux for 60 hrs. The reaction mixture was cooled and then evaporated under reduced pressure. The residue was taken up in 75 mL of CH$_2$Cl$_2$, washed with 50 mL of saturated KF, then 30 mL of brine and dried over Na$_2$SO$_4$. The solvent was evaporated under reduced pressure and the residue was chromatographed on silica gel eluting with 9:1 hexane/ethyl acetate. The product (1.8 g, 70%) was obtained as a light yellow solid. $^1$H NMR (CDCl$_3$) δ 7.1 (s, 1H), 7.2 (m, 7H), 7.35 (m, 8H), 7.6 (t, 1H), 7.7 (s, 1H), 7.9 (t, 2H), 8.35 (d, 1H), 8.5 (1H).

In another method for the preparation of Cp-10, ethyl magnesium bromide (4.0 mL of 3.0 M solution in diethyl ether. 0.012 mole) was added to a solution of 1-trityl-4-iodoimidazole (2.52 g, 0.01 mole) in 100 mL of THF. The reaction mixture was stirred at room temperature for 45 min at which time TLC (70:30 hexane/ethylacetate) indicated the starting material was consumed. Zinc chloride (2.72 g, 0.02 mole) was added and the reaction mixture was stirred for 1 hr. During this time the clear yellowish solution became cloudy white. The isoquinolinyl triflate described above (2.77 g, 0.01 mole) was dissolved in 10 mL of THF and added via syringe. Tetrakis(triphenylphosphine)palladium (0), (0.580 g, 0.0005 mole), was then added and the reaction mixture was heated to reflux. After 3 hrs, TLC indicated that most of the starting triflate was gone. Heating was continued for 16 hrs. The reaction mixture was cooled and 50 mL of saturated $NH_4Cl$ was added. The mixture was extracted with 2×100 mL of $CH_2Cl_2$. The combined organic layers were washed with brine (1×50 mL), dried over $Na_2SO_4$ and evaporated under reduced pressure. The residue was chromatographed on silica gel eluting with 70:30 hexane/ethyl acetate. The product was obtained as a yellowish solid (2.79 g, 64%) and had an identical $^1H$ NMR spectrum to the product obtained by the Stille coupling route described above.

The tritylated isoquinolinylimidazole (obtained by either of the previously described methods) (0.87 g, 0.002 mole) was suspended in 20 mL of methanol and 0.8 mL of concentrated HCl was added. The clear, pale yellow solution was heated at reflux for 5 hrs. The reaction mixture was cooled and the solvent was evaporated under reduced pressure. Methanol was added to the oily residue and evaporated two additional times. The residue was taken up in $CH_2Cl_2$ and filtered. The solid was recrystallized from acetone to yield Cp-10 as a tan crystalline solid. $^1H$ NMR ($CD_3OD$) δ 8.1 (s, 1H), 8.2 (t, 1H), 8.4 (d, 1H), 8.6 (d, 1H), 8.7 (m, 2H), 9.3 (s, 1H,), 10.0 (s, 1H).

Elemental analysis: Calculated for $C_{12}H_9N_3.2HCl$: C, 53.75; H, 4.13; N, 15.67. Found C, 53.54; H, 3.95; N, 15.57.

EXAMPLE 8

Cp-11 was prepared in an analogous manner to Cp-10 and obtained as pale yellow crystals, mp >260° C. $^1H$ NMR ($CD_3OD$): δ 8.2 (m, 1H), 8.3 (s, 1H), 8.4 (d, 1H), 8.6 (d, 1H), 8.7 (s, 1H), 9.3 (s, 1H), 9.7 (2s, 2H).

Elemental analysis: Calculated for $C_{12}H_9N_3.2HCl.0.25H_2O$: C, 52.86; H, 4.07; N, 15.41. Found C, 52.94; H, 4.06; N, 15.44.

Cp-12 was prepared in an analogous manner to Cp-10 and obtained as a yellow solid, mp >260° C. $^1H$ NMR ($CD_3OD$): δ 8.1 (m, 1H), 8.3 (m, 1H), 8.4 (s, 1H), 8.5 (d, 1H), 8.6 (s, 1H), 9.1 (d, 1H), 9.25 (s, 1H), 9.3 (d, 1H).

Elemental analysis: Calculated for $C_{12}H_9N_3.2HCl.0.5H_2O$: C, 52.00; H, 4.00; N, 15.16. Found C, 52.18; H, 4.25; N, 15.16.

Table 2 summarizes the mass spectral data for the compounds of Table 1.

| Cpd# | Mass (calc) | Mass (obs) |
|------|-------------|------------|
| Cp-1 | 173 | 174 |
| Cp-2 | 187 | 188 |
| Cp-3 | 159 | 160 |
| Cp-4 | 238 | 238, 240 |
| Cp-5 | 252 | 252, 254 |
| Cp-6 | 159 | 160 |
| Cp-7 | 235 | 236 |
| Cp-8 | 173 | 174 |
| Cp-9 | 209 | 210 |
| Cp-10 | 195 | 196 |
| Cp-11 | 195 | 196 |
| Cp-12 | 195 | 196 |

What is claimed is:

1. A Compound which is an $\alpha_2$-adrenoceptor agonist of the formula:

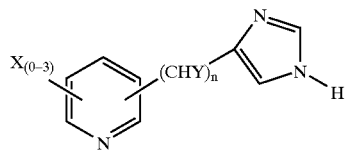

where n is 0, 1, 2;

X is independently selected from the group consisting of $C_{1-4}$alkyl, bromine, chlorine, iodide, trifluoromethyl, $C_{1-4}$alkoxy, $-SO_2NH_2$, nitro, and two adjacent X are optionally fused to form the moiety:

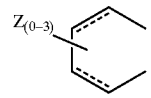

whereby a saturated, partially unsaturated or aromatic six-membered fused ring is formed;

Y is independently selected from the group consisting of hydrogen, hydroxy, $C_{1-4}$alkyl, $C_{1-4}$alkoxy, trifluoromethyl and phenyl; and Z is independently selected from the group consisting of hydroxy, $C_{1-4}$alkyl, bromine, chlorine, iodine, trifluoromethyl, $C_{1-4}$alkoxy, $-SO_2NH_2$ and nitro with the proviso that where n is O, X must be present and X must be said fused moiety, and with the proviso, that where n is 1 or 2, then Y cannot be phenyl.

2. The compound of claim 1 having the formula:

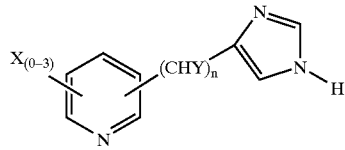

where X, Y, Z and n are dependently selected from the group consisting of:

| position of attachment | X | Y | Z | n |
|---|---|---|---|---|
| 3-pyridyl | 4-Me | H | — | 1 |
| 3-pyridyl | 2-Me | H | — | 2 |
| 3-pyridyl | 5-Me | Me | — | 1 |
| 3-pyridyl | 2-Et | OH | — | 1 |
| 3-pyridyl | 5-isopropyl | OEt | — | 1 |
| 3-pyridyl | 3-Me | H | — | 1 |
| 3-pyridyl | 3-OMe | H | — | 2 |
| 3-pyridyl | 5-Me | H | — | 2 |
| 2-pyridyl | 4-Et | Me | — | 1 |
| 2-pyridyl | 3-Br | H | — | 1 |
| 2-pyridyl | 5-OEt | Me | — | 1 |
| 4-pyridyl | — | H | — | 2 |
| 4-pyridyl | 2-Me | H | — | 1 |
| 6-quinolinyl | fused phenyl | H | — | 1 |
| 5-quinolinyl | fused phenyl | — | — | 0 |
| 7-quinolinyl | fused phenyl | H | 8-Me | 1 |
| 8-quinolinyl | fused phenyl | — | — | 0 |

-continued

| position of attachment | X | Y | Z | n |
|---|---|---|---|---|
| 4-isoquinolinyl | fused phenyl | H | — | 1 |
| 5-isoquinolinyl | fused phenyl | — | — | 0 |
| 6-quinolinyl | fused phenyl | — | 2-Me | 0 |
| 7-isoquinolinyl | fused phenyl | H | 3-Me | 1 |
| 8-quinolinyl | fused phenyl | Me | — | 1 |
| 2-pyridyl | 5,6-fused cyclohexyl | H | — | 1 |
| 2-pyridyl | 5,6-fused cyclohexyl | H | — | 2 |
| 3-pyridyl | 4,5-fused cyclohexyl | H | — | 1 |
| 3-pyridyl | 4,5-fused cyclohexyl | H | — | 2. |

3. The compound of claim 1 having the general formula:

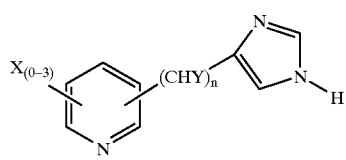

wherein X, Y, and n are dependently selected from the group consisting of:

| Cpd # | position of attachment | X | Y | n |
|---|---|---|---|---|
| Cp-1 | 3-pyridyl | 2-Me | H | 1 |
| Cp-2 | 3-pyridyl | 2-Me | Me | 1 |
| Cp-3 | 3-pyridyl | — | H | 1 |
| Cp-4 | 3-pyridyl | 5-Br | H | 1 |
| Cp-5 | 3-pyridyl | 5-Br | Me | 1 |
| Cp-6 | 2-pyridyl | — | H | 1 |
| Cp-8 | 2-pyridyl | — | H | 2 |
| Cp-9 | 2-quinolinyl | Fused Phenyl | H | 1 |
| Cp-10 | 4-isoquinolinyl | Fused Phenyl | — | 0 |
| Cp-11 | 6-quinolinyl | Fused Phenyl | — | 0 |

-continued

| Cpd # | position of attachment | X | Y | n |
|---|---|---|---|---|
| Cp-12 | 7-quinolinyl | Fused Phenyl | — | 0. |

4. A method for treating a human suffering from the need for analgesia comprising the step of administering an effective amount of a compound which is a suitable α₂-adrenoceptor agonist of the formula:

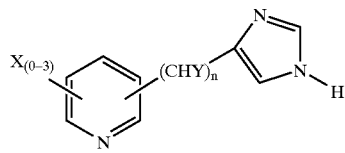

where n is 0, 1, 2;

X is independently selected from the group consisting of $C_{1-4}$alkyl, bromine, chlorine, iodide, trifluoromethyl; $C_{1-4}$alkoxy, —SO₂NH₂, nitro, and two adjacent X are optionally fused to form the moiety:

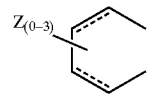

whereby a saturated, partially unsaturated or aromatic six-membered fused ring is formed;

Y is independently selected from the group consisting of hydrogen, hydroxy, $C_{1-4}$alkyl, $C_{1-4}$alkoxy, trifluoromethyl and phenyl; and Z is independently selected from the group consisting of hydroxy, $C_{1-4}$alkyl, bromine, chlorine, iodide, trifluoromethyl, $C_{1-4}$alkoxy, —SO₂NH₂ and nitro with the proviso that where n is 0, X must be present and X must be said fused moiety, and with the proviso, that where n is 1 or 2, then Y cannot be phenyl.

\* \* \* \* \*